United States Patent
Huang

(10) Patent No.: US 12,232,972 B2
(45) Date of Patent: Feb. 25, 2025

(54) INTERSPINOUS STABILIZATION DEVICE

(71) Applicant: Love U Co., Ltd, Kaohsiung (TW)

(72) Inventor: Yu-Hao Huang, Kaohsiung (TW)

(73) Assignee: LOVE U CO., LTD, Kaohsiung (TW)

( * ) Notice: Subject to any disclaimer, the term of this patent is extended or adjusted under 35 U.S.C. 154(b) by 199 days.

(21) Appl. No.: 17/763,923

(22) PCT Filed: Jun. 24, 2021

(86) PCT No.: PCT/CN2021/102041
§ 371 (c)(1),
(2) Date: Mar. 25, 2022

(87) PCT Pub. No.: WO2021/259353
PCT Pub. Date: Dec. 30, 2021

(65) Prior Publication Data
US 2022/0362032 A1    Nov. 17, 2022

(30) Foreign Application Priority Data

Jun. 24, 2020 (CN) .......................... 202010591813.8
Aug. 21, 2020 (CN) .......................... 202010851963.8

(51) Int. Cl.
*A61F 2/44*     (2006.01)
*A61B 17/84*    (2006.01)
*A61F 2/30*     (2006.01)

(52) U.S. Cl.
CPC .......... *A61F 2/4405* (2013.01); *A61B 17/842* (2013.01); *A61F 2002/30166* (2013.01); *A61F 2002/30785* (2013.01)

(58) Field of Classification Search
CPC .......... A61F 2/4405; A61F 2002/30166; A61F 2002/30785; A61F 2002/443; A61B 17/842; A61B 17/7053; A61B 17/7062
See application file for complete search history.

(56) References Cited

U.S. PATENT DOCUMENTS

2018/0008429 A1\* 1/2018 Li ...................... A61B 17/7062
2018/0146989 A1\* 5/2018 Hwang .............. A61B 17/7062

FOREIGN PATENT DOCUMENTS

CN    102551855 A    7/2012
CN    108338856 A    7/2018
(Continued)

OTHER PUBLICATIONS

International Search Report for PCT/CN2021/102041 (PCT/ISA/210) mailed on Sep. 24, 2021.

*Primary Examiner* — Javier G Blanco
(74) *Attorney, Agent, or Firm* — Birch, Stewart, Kolasch & Birch, LLP

(57) ABSTRACT

Provided herein is an interspinous stabilization device, including: a central connection portion, a first side wing, a second side wing, a third side wing, and a fourth side wing. The first side wing extends from the central connection portion in a first direction. The second side wing extends from the central connection portion in the first direction. The third side wing extends from the central connection portion in a second direction opposite to the first direction. The fourth side wing extends from the central connection portion in the second direction. The central connection portion has at least one thread hole. The thread hole extends in a third direction substantially perpendicular to the first direction. The first side wing, the second side wing, the third side wing, and the fourth side wing each have a through hole.

9 Claims, 5 Drawing Sheets

(56) References Cited

FOREIGN PATENT DOCUMENTS

| CN | 111281507 A | 6/2020 |
|---|---|---|
| CN | 213098543 U | 5/2021 |
| WO | WO 2013/052496 A2 | 4/2013 |

\* cited by examiner

INTERSPINOUS STABILIZATION DEVICE

FIELD OF THE INVENTION

The present disclosure relates to an interspinous stabilization device and, more particularly, to an interspinous stabilization device with side wings and through holes thereof.

BACKGROUND OF THE INVENTION

Spine conditions are treated either medicinally or surgically. The medicinal option involves patients' taking medications on a long-term basis to alleviate symptoms, such as pain, rather than cure the spine conditions; drawbacks include psychological changes and side effects. The surgical option is not only invasive but also likely to alter considerably the anatomical structures and functions of the spine. For instance, some spine conditions are treated with spinal fusion, which entails connecting two or more spinal vertebrae by placing bone and/or an implant within the space between two adjacent spinal vertebrae. Spinal fusion is not reversible and can change the range of motion of the spine significantly. Furthermore, indications for spinal fusion are restricted to patients with severe symptoms.

U.S. Pat. No. 8,118,839 discloses a soft interspinous implant which is elastically deformable and thus capable of preventing a spinal process fracture which might otherwise be caused by a hard interspinous implant predisposed to stress concentration on spinal processes. The soft interspinous implant has a bilateral dual-wing structure, i.e., with two identical wing-shaped processes on the left of the interspinous implant and two identical wing-shaped processes on its right. Owing to its bilateral dual-wing structure, the interspinous implant fits well between two adjacent spinal processes. However, the implant is secured by two tethers from the implant around the spinous processes, which is less effective in securing the implant.

Therefore, it is imperative to provide an interspinous stabilization device to overcome the aforesaid drawbacks of the prior art.

SUMMARY OF THE INVENTION

It is an objective of the present disclosure to provide an interspinous stabilization device which is not only inserted simultaneously from behind and from the side of the spinal processes but also comes with a satisfactory bonding mechanism for enhancing implant fixation, reducing the chance of implant detachment, fitting an implant to spinal processes tighter, and thus stabilizing the spine better.

In order to achieve the above and other objectives, the present disclosure provides an interspinous stabilization device comprising a central connection portion, a first side wing, a second side wing, a third side wing, and a fourth side wing. The first side wing extends from the central connection portion in a first direction. The second side wing extends from the central connection portion in the first direction. The third side wing extends from the central connection portion in a second direction opposite to the first direction. The fourth side wing extends from the central connection portion in the second direction. The central connection portion has at least one thread hole. The thread hole extends in a third direction substantially perpendicular to the first direction. The first side wing, the second side wing, the third side wing, and the fourth side wing each have a through hole.

In a specific embodiment, the first side wing, the second side wing, the third side wing, and the fourth side wing each have an outer side surface, a top surface, and an inner side surface, wherein the through holes connect the outer side surfaces to the top surfaces.

In a specific embodiment, the first side wing, the second side wing, the third side wing, and the fourth side wing each have an outer side surface and an inner side surface, wherein the through holes connect the outer side surfaces to the inner side surfaces.

In a specific embodiment, the first side wing and the second side wing are of substantially equal length, whereas the third side wing and the fourth side wing are of substantially equal length.

In a specific embodiment, the first side wing, the second side wing, the third side wing, and the fourth side wing each have an outer side surface and an inner side surface, which are arcuate, and the arcuate shape curves from the outer side surface to the inner side surface.

In a specific embodiment, the first side wing, the second side wing, the third side wing, and the fourth side wing each have a thickness less than that of the central connection portion.

In a specific embodiment, the central connection portion comprises a first surface and a second surface opposing the first surface, the first surface faces the spine upon completion of implantation, and at least one recess is disposed on the second surface.

In a specific embodiment, the first side wing, the second side wing, the third side wing, and the fourth side wing each have a bottom end and a top end, with the bottom ends connected to the central connection portion, and the bottom ends are of greater thickness than the top ends.

In a specific embodiment, the first side wing, the second side wing, the third side wing, and the fourth side wing each have a bottom end and a top end, with the bottom ends connected to the central connection portion, and the bottom ends are of greater width than the top ends.

In a specific embodiment, the interspinous stabilization device is made of biocompatible materials to human body.

In a specific embodiment, the interspinous stabilization device is made of dimethyl silicone, polyurethane or a mixture thereof.

BRIEF DESCRIPTION OF THE DRAWINGS

The accompanying drawings are illustrative of the present disclosure rather than restrictive of the scope of the appended claims.

REFERENCE SIGN

Figure 1:
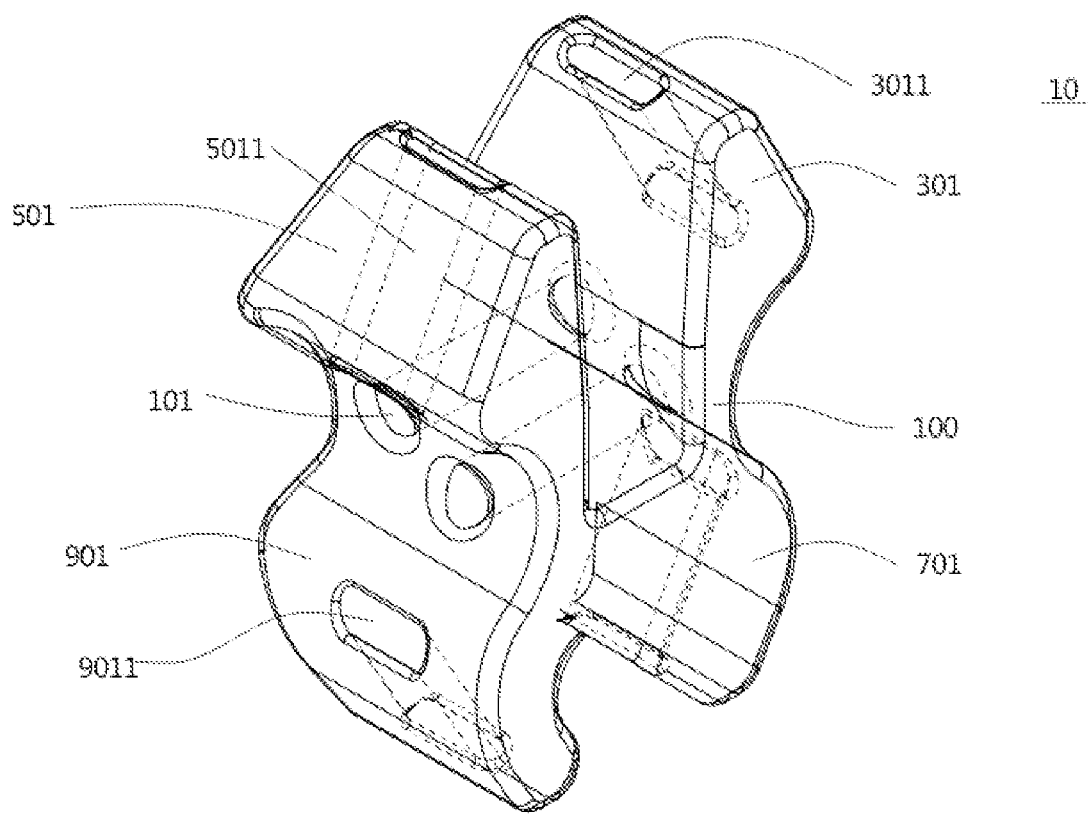
FIG. 1 is a schematic view of an interspinous stabilization device of the present disclosure.

10 Interspinous stabilization device
100 Central connection portion
1005 Second surface
1007 First surface 101, 103 Thread holes
105 First recess
107 Second recess
301 First side wing
3011 First through hole
3013 Outer side surface
3015 Top surface
3017 Inner side surface
501 Second side wing
5011 Second through hole
701 Third side wing
7011 Third through hole
901 Fourth side wing
9011 Fourth through hole

DETAILED DESCRIPTION OF THE EMBODIMENTS

Technical features, inclusive of specific features, of the present disclosure are disclosed in the appended claims. The technical features of the present disclosure are illustrated by embodiments, depicted by accompanying drawings, and described in detail below. The disclosure herein can be comprehended and implemented by persons skilled in the art. All equivalent changes and modifications made by persons skilled in the art to the embodiments of the present disclosure without departing from concepts embodied in the present disclosure must be deemed falling within the scope of the appended claims.

Unless otherwise specified, definitions for all technical and scientific terms used herein are well known among persons skilled in the art. Unless otherwise specified, singular determiners, such as "a", "one", "the" and the like, must be interpreted in such a manner to include their plural forms. Unless otherwise specified, conjunctions, such as "or" and "and", also mean "or/and". The verbs "include" and "comprise" are each an open-ended transition. The aforesaid definitions are directed to terminology rather than intended to limit the subject matter of the present disclosure. Unless otherwise specified, all raw materials disclosed by the present disclosure are commercially-available and accessible.

Ordinal numbers, such as "first" and "second," used herein are only intended to specify disclosed components but do not necessarily imply the order of the components in any execution process, sequence, or process flow. The ordinal numbers are intended to distinguish components which bear the same name.

Position-related terms, such as "on", "above", "over" and the like, used herein may refer to two components in direct contact with each other or refer to two components not in direct contact with each other.

Referring to FIGS. 1-4, the present disclosure provides an interspinous stabilization device 10, comprising a central connection portion 100, a first side wing 301, a second side wing 501, a third side wing 701, and a fourth side wing 901.

The first side wing 301 extends from the central connection portion 100 in a first direction. The second side wing 501 extends from the central connection portion 100 in the first direction. The third side wing 701 extends from the central connection portion 100 in a second direction opposite to the first direction. The fourth side wing 901 extends from the central connection portion 100 in the second direction. Therefore, the first side wing 301 and the second side wing 501 extend from the central connection portion 100 in the same direction, whereas the third side wing 701 and the fourth side wing 901 extend from the central connection portion 100 in the same direction. The extension direction of the first side wing 301 and the second side wing 501 and the extension direction of the third side wing 701 and the fourth side wing 901 are opposite.

The central connection portion 100 has at least one thread hole. In the figures, the central connection portion 100 has two thread holes 101, 103, but the present disclosure is not limited thereto. In a variant embodiment, the central connection portion 100 has one thread hole or more than two thread holes. The thread holes are arranged lengthwise (i.e., along the length direction of the interspinous stabilization device 10), widthwise (i.e., along the width direction of the interspinous stabilization device 10), or obliquely. The thread holes 101, 103 extend in a third direction substantially perpendicular to the first direction. Therefore, as shown in FIG. 2, the thread holes 101, 103 extend in a direction substantially perpendicular to the extension directions of the side wings 301, 501, 701, 901 and perpendicular to the length direction of the interspinous stabilization device 10.

The first side wing 301, the second side wing 501, the third side wing 701, and the fourth side wing 901 each have a through hole.

Specifically, the first side wing 301 has a first through hole 3011. The second side wing 501 has a second through hole 5011. The third side wing 701 has a third through hole 7011. The fourth side wing 901 has a fourth through hole 9011.

Figure 2:
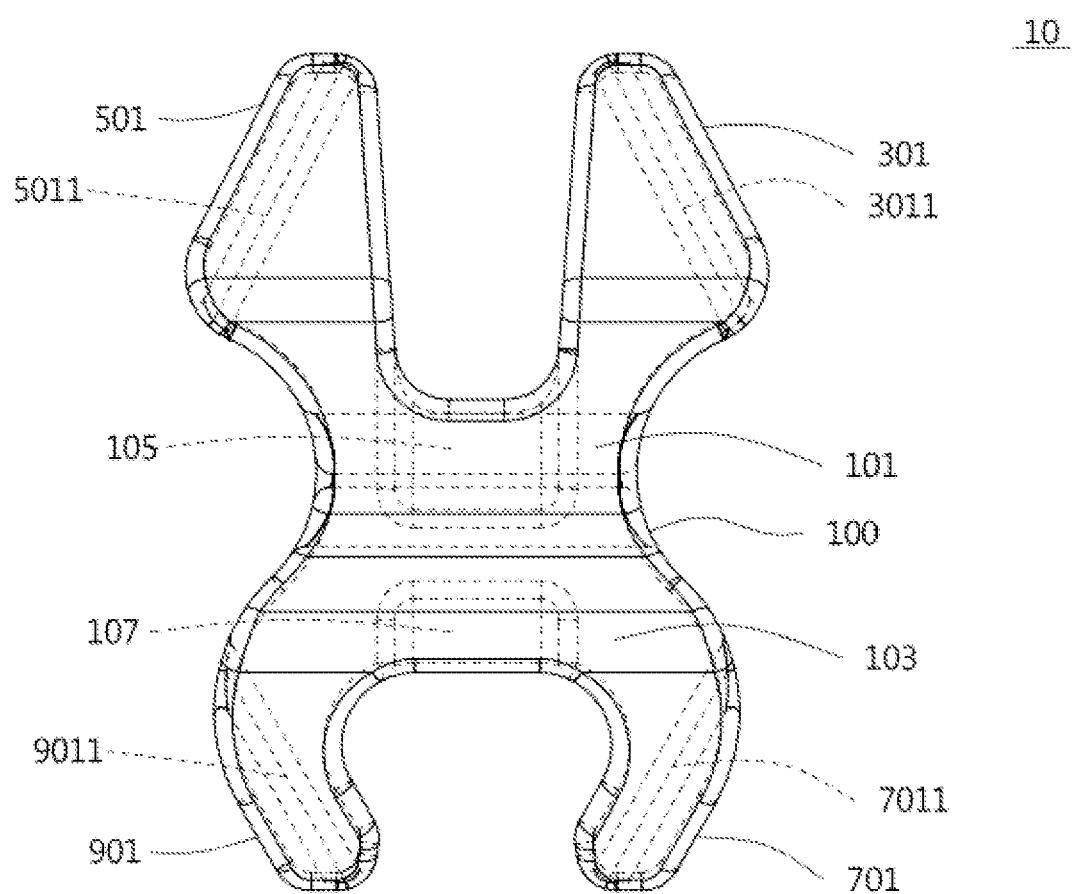
FIG. 2 is a front view of the interspinous stabilization device of the present disclosure.
Figure 3:
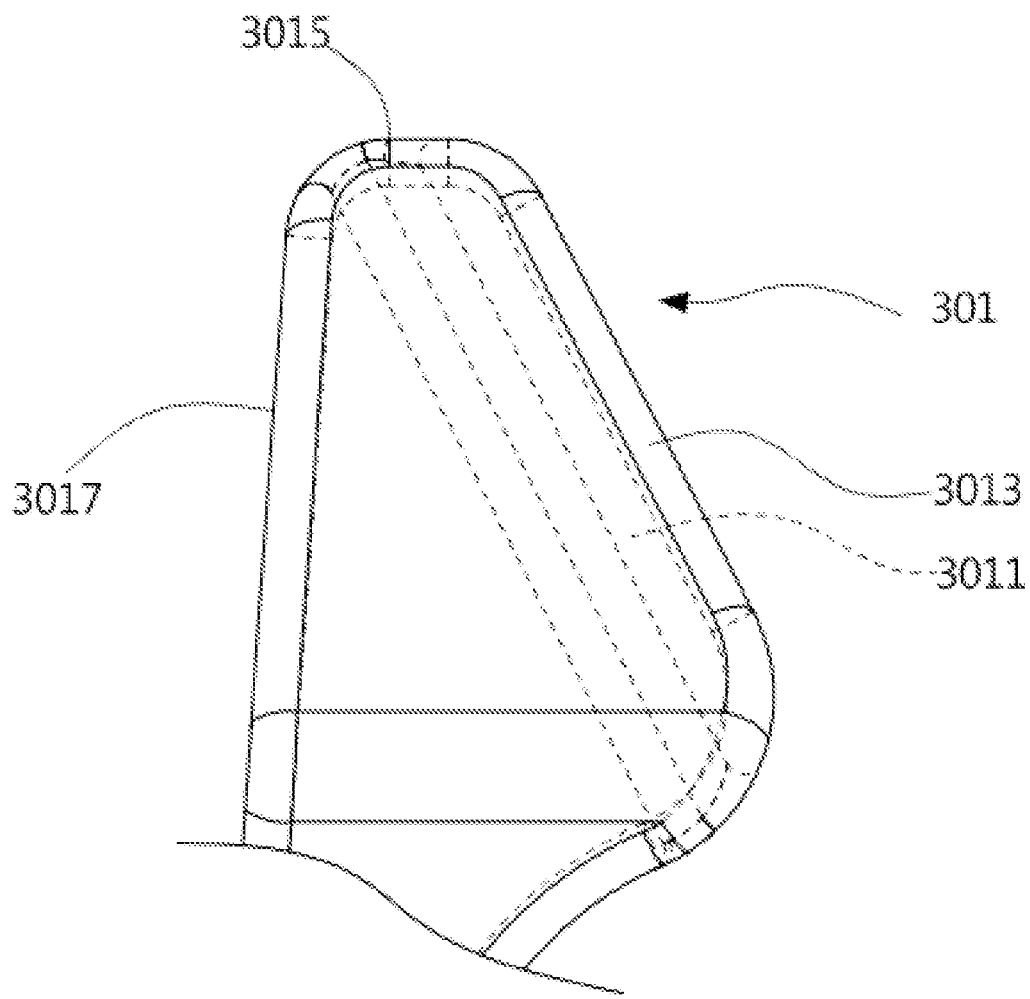
FIG. 3 is a schematic view of a side wing of the interspinous stabilization device of the present disclosure.

In the embodiment illustrated by FIGS. 2, 3, the side wings 301, 501, 701, 901 each have an outer side surface, a top surface, and an inner side surface. As shown in FIG. 3, the first side wing 301 has an outer side surface 3013, a top surface 3015, and an inner side surface 3017. The inner side surface 3017 faces one surface of another side wing. The outer side surface 3013 opposes another surface of the inner side surface 3017. The top surface 3015 connects the outer side surface 3013 and the inner side surface 3017. In this embodiment, the first through hole 3011 connects the outer side surface 3013 and the top surface 3015.

In another embodiment not shown, each through hole connects the corresponding outer side surface and the corresponding inner side surface of the corresponding side wing.

In another embodiment not shown, each side wing does not have any top surface but has an outer side surface and an inner side surface which are not only connected but are also connected to a through hole.

In a specific embodiment, the first side wing 301 and the second side wing 501 are of substantially equal length. The third side wing 701 and the fourth side wing 901 are of substantially equal length. In another specific embodiment, the length of the first side wing 301 and the second side wing 501 and the length of the third side wing 701 and the fourth side wing 901 are equal or unequal.

In a specific embodiment, the first side wing 301, the second side wing 501, the third side wing 701, and the fourth side wing 901 each have a thickness less than the thickness of the central connection portion 100. In a preferred embodiment, the first side wing 301, the second side wing 501, the third side wing 701, and the fourth side wing 901 each have a bottom end and a top end. The bottom ends are connected to the central connection portion 100. The thickness of the bottom ends is greater than the thickness of the top ends. Therefore, among all the constituent elements of the interspinous stabilization device 10, the central connection portion 100 has the greatest thickness. The thickness of the central connection portion 100 is greater than or equal to the thickness of the bottom ends of the side wings. The thickness of the side wings decreases gradually from the bottom ends toward the top ends, such that the bottom ends have the least thickness.

In a specific embodiment, the first side wing 301, the second side wing 501, the third side wing 701, and the fourth side wing 901 each have an outer side surface and an inner side surface, both of which are arcuate. The arcuate shape curves from the outer side surface to the inner side surface. Therefore, in this embodiment, regarding the inner side surfaces of the side wings, the distance between the bottom ends of the opposing inner side surfaces is greater than the distance between the top ends of the opposing inner side surfaces.

In this embodiment, for the inner side surfaces of the side wings, the distance between the bottom ends of the inner side surfaces opposite to each other is greater than or equal to the distance between the top ends of the inner side surfaces opposite to each other.

In another variant embodiment, the first side wing 301, the second side wing 501, the third side wing 701, and the fourth side wing 901 each have a bottom end and a top end. The bottom ends are connected to the central connection portion 100, and the width of the bottom ends is greater than the width of the top ends. Regarding the first side wing 301 and the second side wing 501 in the embodiment illustrated by FIG. 2, their bottom ends have greater thickness than their top ends. Therefore, in the embodiment illustrated by FIG. 2, the side wings 301, 501 are triangular in shape in a front view. However, in a variant embodiment, the side wings are arcuate.

Figure 4:
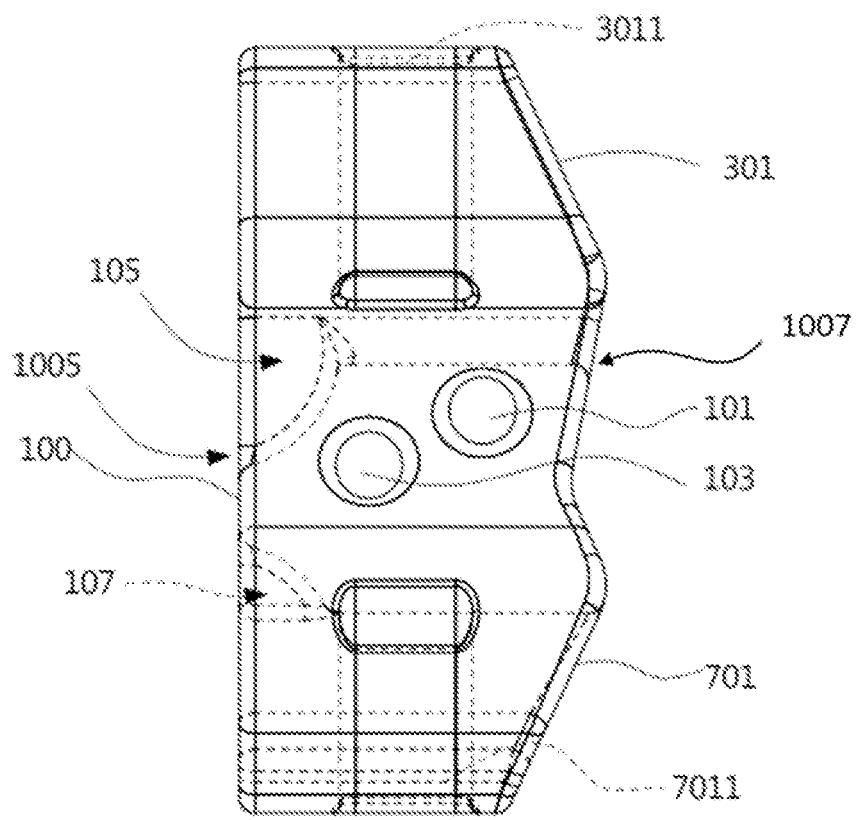
FIG. 4 is a lateral view of the interspinous stabilization device of the present disclosure.

As shown in FIG. 4, the central connection portion 100 has a first surface 1007 and a second surface 1005 opposing the first surface 1007. The first surface 1007 faces the spine upon completion of implantation. At least one recess is disposed on the second surface 1005. In the embodiment illustrated by FIG. 4, the second surface 1005 comprises a first recess 105 and a second recess 107. The first recess 105 is disposed between the first side wing 301 and the second side wing 501. The second recess 107 is disposed between the third side wing 701 and the fourth side wing 901. The first recess 105 extends in the second direction. The second recess extends in the first direction.

Furthermore, the interspinous stabilization device 100 is made of a biocompatible material, including but not limited to dimethyl silicone, polyurethane, or a mixture thereof.

Figure 5:
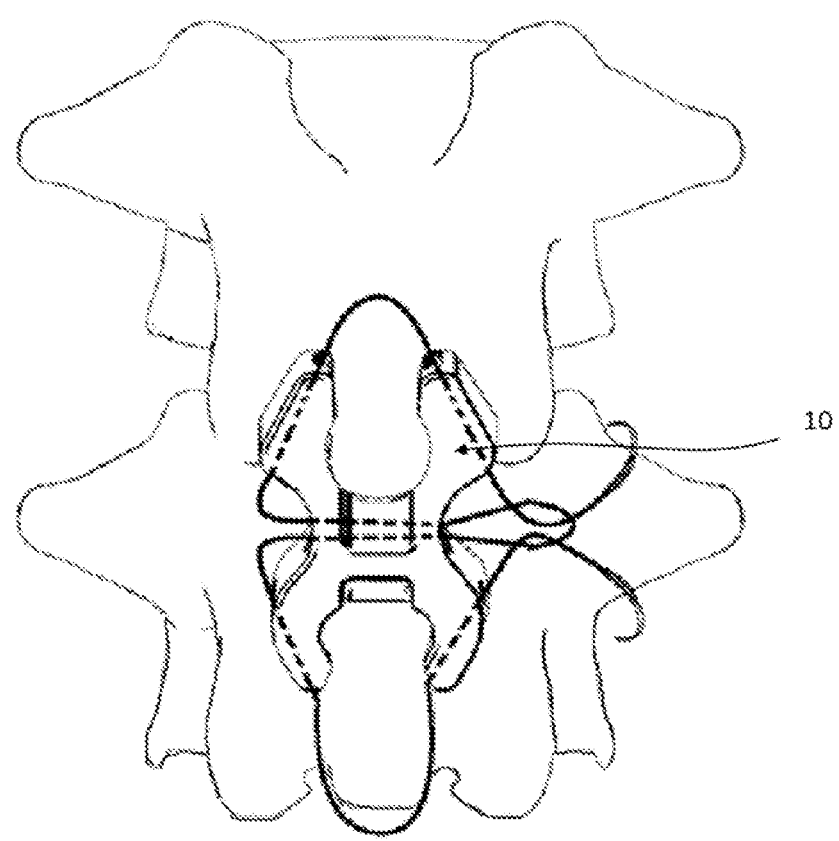
FIG. 5 is a schematic view of the interspinous stabilization device fixed to the spine according to the present disclosure.

FIG. 5 is a schematic view of the interspinous stabilization device 100 fixed to the spine according to the present disclosure. In the present disclosure, the interspinous stabilization device 100 is fixed to the spine with a tether. As shown in FIG. 5, one end of a tether passes through a thread hole, the second through hole and the first through hole sequentially, whereas the other end of the tether passes through another thread hole, the fourth through hole and the third through hole sequentially, such that the two ends of the tether are fixed to a clasp, thereby allowing the interspinous stabilization device 100 to be fixed to the spine with the clasp.

The present disclosure is disclosed above by embodiments. However, persons skilled in the art should understand that the embodiments are illustrative, rather than restrictive, of the present disclosure. Persons skilled in the art can make various changes and replacements to the aforesaid embodiments without varying the technical features disclose herein. According to the embodiments, the present disclosure is subject to various changes without affecting its implementation. The scope of the present disclosure is defined by the appended claims.

What is claimed is:

1. An interspinous stabilization device, comprising:
    a central connection portion having at least one thread hole;
    a first side wing extending from the central connection portion in a first direction;
    a second side wing extending from the central connection portion in the first direction;
    a third side wing extending from the central connection portion in a second direction opposite to the first direction; and
    a fourth side wing extending from the central connection portion in the second direction,
    wherein the thread hole extends in a third direction perpendicular to the first direction,
    wherein the first side wing, the second side wing, the third side wing, and the fourth side wing each have a through hole,
    wherein the first side wing, the second side wing, the third side wing, and the fourth side wing each have a bottom end connected to the central connection portion, a top end defining an endmost surface, an inner side surface, and an outer side surface,
    wherein the through hole of each of the first side wing, the second side wing, the third side wing and the fourth side wing extends within the respective side wing from the respective endmost surface toward the central connection portion, and oriented radially outward with respect to a central axis extending in a length direction of the interspinous stabilization device perpendicular to the third direction, and
    wherein each of the through holes extends parallel to the outer side surface of the corresponding side wing.

2. The device of claim 1, wherein the first side wing and the second side wing are of equal length, and the third side wing and the fourth side wing are of equal length.

3. The device of claim 1, wherein the first side wing, the second side wing, the third side wing, and the fourth side wing each have an arcuate shape curving from the outer side surface to the inner side surface.

4. The device of claim 1, wherein the first side wing, the second side wing, the third side wing, and the fourth side wing each have a thickness less than that of the central connection portion.

5. The device of claim 1, wherein the central connection portion comprises a first surface and a second surface opposing the first surface, the first surface faces the spine upon completion of implantation, and at least one recess is disposed on the second surface.

6. The device of claim 1, wherein the bottom ends are of greater thickness than the top ends.

7. The device of claim 1, wherein the bottom ends are of greater width than the top ends.

8. The device of claim 1, wherein the interspinous stabilization device is made of biocompatible materials to human body.

9. The device of claim 1, wherein the interspinous stabilization device is made of dimethyl silicone, polyurethane or a mixture thereof.

* * * * *